United States Patent
Amling et al.

(10) Patent No.: US 9,357,902 B2
(45) Date of Patent: Jun. 7, 2016

(54) UPDATEABLE ENDOSCOPIC VIDEO IMAGING SYSTEM WITH UNIFIED ELECTRO-OPTIC CABLE

(75) Inventors: Marc R. Amling, Santa Barbara, CA (US); David Chatenever, Santa Barbara, CA (US); Bruce L. Kennedy, Santa Barbara, CA (US); Barry A. Mirrer, Santa Barbara, CA (US)

(73) Assignee: Karl Storz Imaging, Inc., Goleta, CA (US)

( * ) Notice: Subject to any disclaimer, the term of this patent is extended or adjusted under 35 U.S.C. 154(b) by 1875 days.

(21) Appl. No.: 12/130,660

(22) Filed: May 30, 2008

(65) Prior Publication Data

US 2008/0225134 A1 Sep. 18, 2008

Related U.S. Application Data

(60) Division of application No. 11/032,266, filed on Jan. 10, 2005, now Pat. No. 7,520,853, which is a continuation-in-part of application No. 10/034,271, filed on Dec. 28, 2001, now Pat. No. 6,960,161.

(51) Int. Cl.
*A62B 1/04* (2006.01)
*A61B 1/00* (2006.01)
(Continued)

(52) U.S. Cl.
CPC ......... *A61B 1/00124* (2013.01); *A61B 1/00119* (2013.01); *A61B 1/00126* (2013.01); *A61B 1/045* (2013.01); *G02B 6/4292* (2013.01); *G02B 6/4298* (2013.01)

(58) Field of Classification Search
CPC . G06F 3/013; G06F 3/0304; G06F 17/30268; G06F 3/012; G06F 3/017; G06F 3/03545; G06F 3/0386; G06F 3/1205; G06F 3/1222; G06F 3/1238; G06F 3/1292; G06F 17/30873; G06F 2203/04806
USPC .............. 348/65, 45, 272; 600/112, 109, 182; 700/19
See application file for complete search history.

(56) References Cited

U.S. PATENT DOCUMENTS 4,343,300 A * 8/1982 Hattori ........................ 600/109
4,356,534 A   10/1982 Hattori
4,402,313 A    9/1983 Yabe
(Continued)

FOREIGN PATENT DOCUMENTS

DE   3808011 A1   9/1988
JP   5277065 A   10/1993
(Continued)

OTHER PUBLICATIONS

European Search Report, dated Jan. 7, 2004, 3 pages.
(Continued)

*Primary Examiner* — Gims Philippe
(74) *Attorney, Agent, or Firm* — Whitmyer IP Group LLC

(57) ABSTRACT

A control unit is detachably coupled to a camera and receptive of the imaging data with a plurality of data processing instructions being stored on the camera and/or the control unit such that when the camera is coupled to the control unit, the plurality of data processing instructions transfer the imaging data from the camera to the control unit. The data processing instructions being field upgradeable with a portable upgrading module which may couple directly to either the camera and/or the control unit.

19 Claims, 11 Drawing Sheets

(51) Int. Cl.
*A61B 1/045* (2006.01)
*G02B 6/42* (2006.01)

(56) References Cited

U.S. PATENT DOCUMENTS

| | | | |
|---|---|---|---|
| 4,651,201 A * | 3/1987 | Schoolman | 348/45 |
| 4,667,230 A | 5/1987 | Arakawa et al. | |
| 4,905,082 A | 2/1990 | Nishigaki et al. | |
| 4,963,960 A | 10/1990 | Takami | |
| 5,007,408 A | 4/1991 | Ieoka | |
| 5,010,876 A | 4/1991 | Henley et al. | |
| 5,239,983 A | 8/1993 | Katsurada | |
| 5,242,315 A | 9/1993 | O'Dea | |
| 5,311,859 A | 5/1994 | Monroe et al. | |
| 5,419,717 A | 5/1995 | Abendschein et al. | |
| 5,509,096 A | 4/1996 | Easley | |
| 5,569,158 A | 10/1996 | Suzuki et al. | |
| 5,575,757 A | 11/1996 | Kennedy et al. | |
| 5,627,583 A | 5/1997 | Nakamura et al. | |
| 5,631,702 A * | 5/1997 | Miwada | 348/272 |
| 5,702,345 A | 12/1997 | Wood et al. | |
| 5,716,323 A | 2/1998 | Lee | |
| 5,751,341 A * | 5/1998 | Chaleki et al. | 348/65 |
| 5,852,697 A | 12/1998 | Williams et al. | |
| 5,896,166 A | 4/1999 | D'Alfonso et al. | |
| 5,974,464 A | 10/1999 | Shin et al. | |
| 5,976,070 A | 11/1999 | Ono et al. | |
| 6,110,107 A * | 8/2000 | Bellahsene et al. | 600/182 |
| 6,133,941 A | 10/2000 | Ono | |
| 6,261,226 B1 | 7/2001 | McKenna et al. | |
| 6,293,910 B1 | 9/2001 | Yamakita et al. | |
| 6,313,868 B1 | 11/2001 | D'Alfonso et al. | |
| 6,388,702 B1 | 5/2002 | Konomura et al. | |
| 6,494,826 B1 | 12/2002 | Chatenever et al. | |
| 6,503,195 B1 | 1/2003 | Keller et al. | |
| 6,554,765 B1 | 4/2003 | Yarush et al. | |
| 6,638,212 B1 | 10/2003 | Oshima | |
| 6,960,161 B2 * | 11/2005 | Amling et al. | 600/112 |
| 6,985,780 B2 * | 1/2006 | Hudson et al. | 700/19 |
| 7,018,331 B2 * | 3/2006 | Chang et al. | 600/182 |
| 7,212,227 B2 | 5/2007 | Amling et al. | |
| 7,520,853 B2 * | 4/2009 | Amling et al. | 600/109 |
| 2001/0024233 A1 | 9/2001 | Urisaka et al. | |
| 2002/0161279 A1 | 10/2002 | Luloh et al. | |
| 2003/0097042 A1 | 5/2003 | Eino | |
| 2003/0125606 A1 | 7/2003 | Amling et al. | |

FOREIGN PATENT DOCUMENTS

| | | |
|---|---|---|
| JP | 2000245681 A | 9/2000 |
| JP | 2001281557 A | 10/2001 |
| JP | 2003084994 A | 3/2003 |
| JP | 2003296116 A | 10/2003 |
| JP | 2004033726 A | 2/2004 |

OTHER PUBLICATIONS

Texas Instruments Incorporated, Interface Circuits for TIA/EIA-644 (LVDS) Design Notes, Mixed-Signal Products, Copyright Nov. 1988, SLLA038, 20 pages.

* cited by examiner

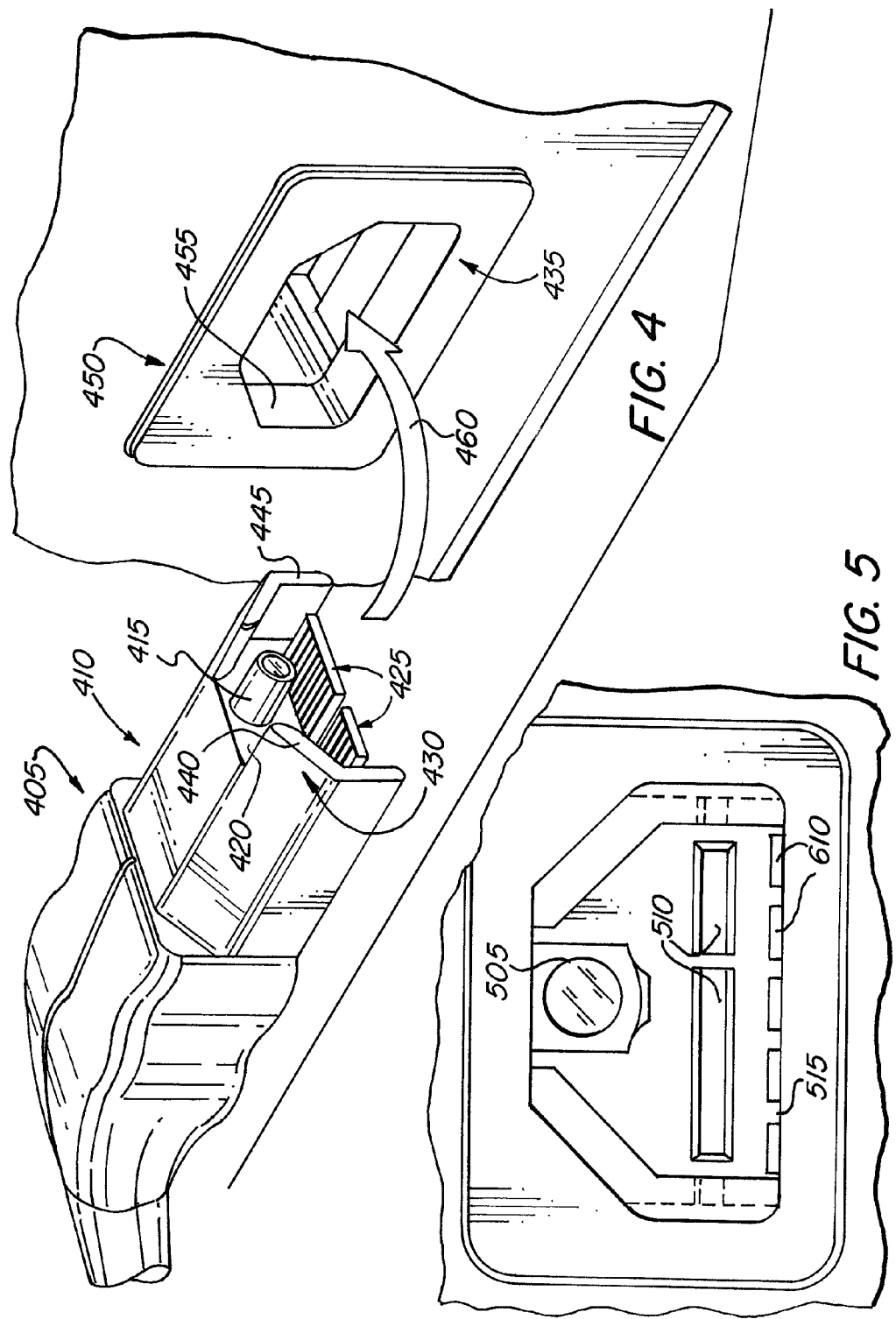

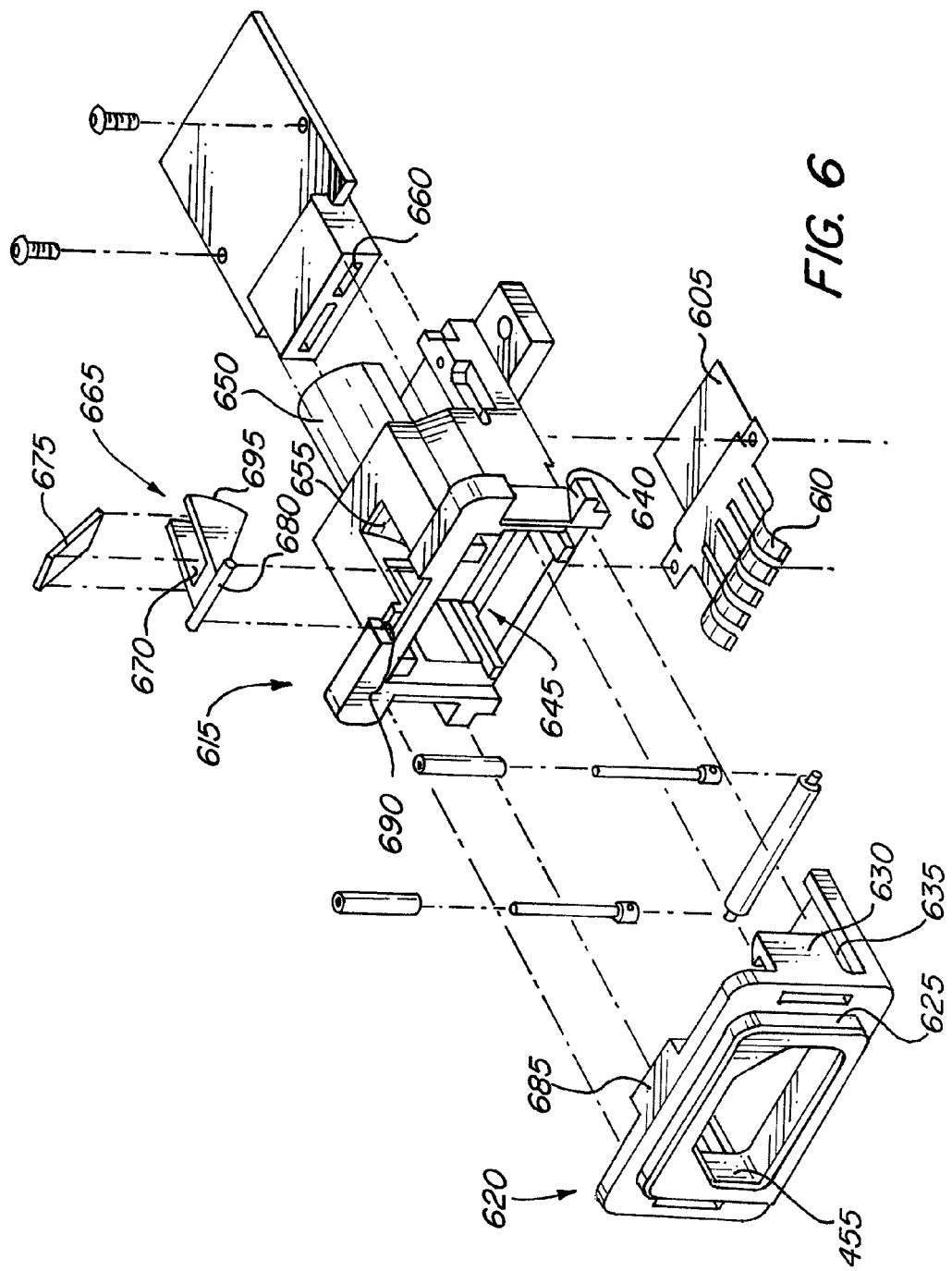

UPDATEABLE ENDOSCOPIC VIDEO IMAGING SYSTEM WITH UNIFIED ELECTRO-OPTIC CABLE

CROSS-REFERENCE TO RELATED APPLICATIONS

This application is a divisional of U.S. patent application Ser. No. 11/032,266, filed Jan. 10, 2005, now U.S. Pat. No. 7,520,853 issued on Apr. 21, 2009, which is a continuation-in-part of U.S. patent application Ser. No. 10/034,271, filed on Dec. 28, 2001, now U.S. Pat. No. 6,960,161, both of which are incorporated herein in their entireties.

FIELD OF THE INVENTION

This application relates to an video imaging system and camera assembly including a field-upgradeable camera configured to generate computer executable image data in response to a set of prescribed imaging functions characteristic of the camera, and an updating module for upgrading the camera in the field.

BACKGROUND OF THE INVENTION

The field of video endoscopy, to which the present invention generally relates, includes medical diagnostic and therapeutic disciplines that utilize endoscopes to penetrate and view otherwise inaccessible body cavities utilizing minimally invasive surgical procedures. Coupling of video imaging cameras (incorporating solid-state imagers) to endoscopes, for image reproduction, has become standard within the field. Endoscopic video cameras are most advantageously small and lightweight for ease of use by medical personnel, and typically incorporate either single or multiple solid-state imagers. Some special purpose endoscopes have integrated (built-in) solid-state imagers, which do not facilitate direct viewing of internal body cavities by medical personnel without an accompanying video imaging system and display. To achieve the desired size and weight, camera head and/or integrated endoscope-camera assembly electronics are typically separated physically from the majority of circuitry required to process and output high-quality, color video images.

In known video imaging systems, interconnection between a camera control unit ("CCU") and a camera is achieved by means of a cable, with usually one cable end permanently fixed to the camera head, while the other cable end is detachably connected to the CCU using a connector.

Most cables for endoscopic video cameras include a fiber optic light guide for illumination, the fiber optic light guide being separately distinct from the cable transmitting electronic video signals.

Existing interconnections between cameras and CCUs typically comprise dedicated parallel wires to provide greater data carrying capacity. It is meant by "dedicated parallel wires" that each specific signal is transmitted by means of an individual wire, either single for power and control signals or shielded coax for image data, between a camera head and CCU. As video imaging systems develop, CCUs are becoming programmable for compatibility with various types of camera heads, adding new control features and the ability to process different types of video signals.

One problem with current camera systems is that the camera is provided with one set of operating instructions. These instructions however may not be appropriate for many differing procedures. Presently, the physician must choose the camera based upon the type of procedure he or she is going to perform. This is highly undesirable because many more cameras must be stocked for differing procedures than would otherwise be required. This leads to higher inventory and maintenance costs. In addition, a proprietary camera for particular procedures or sets of procedures is disadvantageous because the wrong camera for a particular procedure could be selected.

Another problem with current video systems is that when shipped from the factory cameras are equipped with current software identifying the camera and providing for configuration and camera functionality, however, this software quickly becomes outdated and must be updated as new functionality becomes available. The current updating process is burdensome because the camera must be taken out of service, shipped to the factory where updated software is installed and then is shipped back to the user. This process is highly undesirable because it requires that the user and/or institution have multiple cameras for use when frequent updates must be applied to the existing cameras.

What is desired then is a system and method that allows a single camera to be optimized and utilized for most procedures.

It is further desired to provide a system and method for quickly and easily updating camera software whether the software resides on the CCU and/or the camera.

SUMMARY OF THE INVENTION

These and other objects are achieved by the provision of a system and method where a camera assembly comprises a camera configured to generate electronic image data. A control unit is detachably coupled to the camera and receptive of the image data. A first set of data processing instructions are stored in the control unit for processing the image data. A second set of data processing instructions stored in the camera for processing the image data. At least a third set of data processing instructions are interchangeable with the second set of data processing instructions and are operative in processing the image data, where the third set of data processing instructions is different from the second set of data processing instructions. It is contemplated that any number of instructions sets may be utilized by the camera depending upon the application and procedure. In one advantageous embodiment the multiple instruction sets for the camera are stored remotely from the camera where the correct instruction set can be loaded onto the camera as needed.

The first and second set of prescribed image functions characteristics of the camera in one embodiment may comprise for instance, camera exposure, camera focus, camera zoom, camera rotation or photo dynamic diagnosis.

The second set of data processing instructions and third set of data processing instructions may be interchangeable to operate the camera with both sets being compatible with the first set of data processing instructions on the control unit. Thus, should the camera be used in different environments, the interchangeable data processing instructions can be changed as needed to suit the environment. For example, if the camera is used in arthroscopic surgery, it may be desired to have the second set of data processing instructions operative on the camera. However, if the camera is used in intestinal surgery, it may be desired to have the third set of data processing instructions operative on the camera.

Therefore, essentially any camera is able to operate with essentially any version of the data processing instructions. Depending upon the data processing instructions currently loaded on the camera, the desired functionality can be selected to ensure proper operation of the camera for the selected procedure. With the camera and control unit decoupled, the control unit executes only the data processing instructions stored thereon. However, when the camera and control unit are coupled to one another, the image data is downloaded from the camera to the control unit for processing. This allows each camera to provide temporary fixes or updates to the data processing instructions stored in the control unit without having to send the control unit for service.

The data processing instructions are architected in four layers:
1) an application layer which is a top level set of instructions that performs the high level objectives of the camera;
2) a hardware abstraction layer which provides a standardized interface between the application layer and device drivers;
3) device drivers which are data processing instructions that directly manipulates hardware; and
4) a hardware layer which is the hardware itself, manipulated by the device drivers.

The data processing instructions in the control unit facilitate the downloading of application software and field programmable gate array (FPGA) instructions from a camera that is plugged into a camera chassis. Cameras may be plugged in or unplugged at any time, including when the camera is on. The presence or absence of a camera will automatically be detected.

The data processing instructions are capable of receiving essentially any camera at any time. This means that the control unit and the data processing instructions thereon must be capable of detecting and operating with substantially any camera. This includes single chip, three chip and progressive scan CCDs, coupled with NTSC, PAL or other video standards.

When a camera is connected to a control unit, the data processing instructions download the executable image data located on the camera. This executable image will work in concert with that in the control unit to provide for the overall capability required for the video imaging system. With no camera attached, the control unit will provide basic "unconnected" related functionality such as limited user menus.

The data processing instructions in the control unit are capable of configuring both a formatter and a processor FPGA. When no camera is plugged into the control unit (including when a camera is plugged in but is subsequently removed), the data processing instructions in the control unit download the base FPGA configuration code to the FPGA. When a camera is plugged in, the data processing instructions in the control unit reconfigures the FPGA(s) by reprogramming them with new FPGA code stored in the camera.

The data processing instructions in the control unit are capable of downloading new instructions from the camera head. Once complete, the downloaded code is linked with the data processing instructions in the control unit, extending the capabilities to include camera-specific applications. The camera instructions, at a minimum, include the application instructions to handle camera-specific items. Examples of this may include enhancement, brightness, and shutter functions, etc. Data processing instruction modules in the control unit have the ability to extend, modify, and/or replace functionality each time a camera is plugged into or unplugged from the control unit chassis.

The data processing instructions in the control unit provide for new software drivers downloaded from the camera. Upon removal of the camera, the newly downloaded software drivers are unloaded.

In one advantageous embodiment a camera assembly is provided comprising a camera adapted to generate image data and a control unit detachably coupled to the camera and receptive of the image data. The camera assembly further comprises camera specific data processing instructions specific to the camera stored on the camera and control unit data processing instructions stored on the control unit. The camera assembly is provided such that when the camera is coupled to the control unit, the camera specific data processing instructions on the camera cooperate with the control unit data processing instructions on the control unit to transfer and process the image data from the camera to the control unit; and the image data is stored on both the camera and the control unit.

In another advantageous embodiment a camera assembly is provided comprising a camera adapted to generate image data and a control unit detachably coupled to the camera and receptive of the image data. The camera assembly further comprises camera specific data processing instructions specific to the camera stored on the camera, control unit data processing instructions stored on the control unit, and a light source for generating illuminating light. The camera assembly still further comprises a cable coupled between the camera and the control unit including a light guide coupled to the light source for transmitting the illuminating light from the light source to an object, and a channel for transmitting the image data from the camera to the control unit. The camera assembly is provided such that when the camera is coupled to the control unit, the camera specific data processing instructions on the camera cooperate with the control unit data processing instructions on the control unit to transfer and process the image data from the camera to the control unit.

In still another advantageous embodiment a camera assembly is provided comprising a camera adapted to generate image data representative of an image and a control unit detachably coupled to the camera and receptive of the image data. The camera assembly further comprises a plurality of camera specific data processing instructions, and control unit data processing instructions. The camera assembly is provided such that when the camera is coupled to the control unit, the control unit selects the correct camera specific data processing instructions to use based on identification of the connected camera.

In yet another advantageous embodiment a camera system is provided comprising a camera adapted to generate image data representative of an image, and a control unit detachably coupled to the camera and receptive of the image data. The camera assembly further comprises a plurality of camera specific data processing instructions, control unit data processing instructions, and a light source for generating illuminating light. The camera assembly still further comprises a cable coupled between the camera and the control unit including a light guide coupled to the light source for transmitting the illuminating light from the light source to an object, and a channel for transmitting the image data from the camera to the control unit. The camera assembly is provided such that when the camera is coupled to the control unit, the control unit selects the correct camera specific data processing instructions to use based on identification of the connected camera.

In still another advantageous embodiment a video imaging system is provided comprising a camera for generating image data, a control unit for controlling the camera, and a cable for connecting the camera to the control unit, the cable including a channel for transmitting camera operating information between the camera and the control unit. The camera assembly further comprises a light guide for transmitting illuminating light from a light source to the camera, where the cable longitudinally engages the camera so as to direct light longitudinally and completely through the camera.

In yet another advantageous embodiment a video imaging system is provided comprising a camera, a control unit, and a cable coupling the camera to the control unit. The cable is enclosed in a single protective jacket and includes at least one channel for transmitting information between the camera and the control unit, and a light guide for transmitting illuminating light to the camera. The video imaging system is provided such that the cable longitudinally engages the camera so as to direct the illuminating light longitudinally and completely through the camera.

In still another advantageous embodiment a portable system for upgrading camera operational parameters in the field is provided comprising, a field programmable camera, a set of operation parameters for controlling the camera, and a data set indicative of a level of features a user is entitled to utilize in connection with the camera. The portable system further comprises a system storage accessible by the camera for storing the set of operation parameters and the data set, a portable upgrading module for updating the set of operation parameters and a module storage for storing operation parameter upgrades and data sets indicative of levels of operation parameter features a user is entitled to use. The portable system still further comprises a communications link established between the module and the camera, and software operating on the module for reading and updating the set of operation parameters based upon the data set.

In yet another advantageous embodiment a portable system for upgrading control unit operational parameters in the field is provided comprising, a field programmable camera, a set of operation parameters for controlling the control unit, and a data set indicative of a level of features a user is entitled to utilize in connection with the control unit. The portable system further comprises a system storage accessible by the control unit for storing the set of operation parameters and the data set, a portable upgrading module for updating the set of operation parameters and a module storage for storing operation parameter upgrades and data sets indicative of levels of operation parameter features a user is entitled to use. The portable system still further comprises a communications link established between the module and the control unit, and software operating on the module for reading and updating the set of operation parameters based upon the data set.

The invention and its particular features and advantages will become more apparent from the following detailed description considered with reference to the accompanying drawings.

BRIEF DESCRIPTION OF THE DRAWINGS

FIG. 4 is a depiction of the connector assembly to be advanced into the receptacle.

FIG. 5 is a front section view of the receptacle.

FIG. 6 is an assembly drawing of the receptacle.

DETAILED DESCRIPTION OF THE INVENTION

Figure 1:
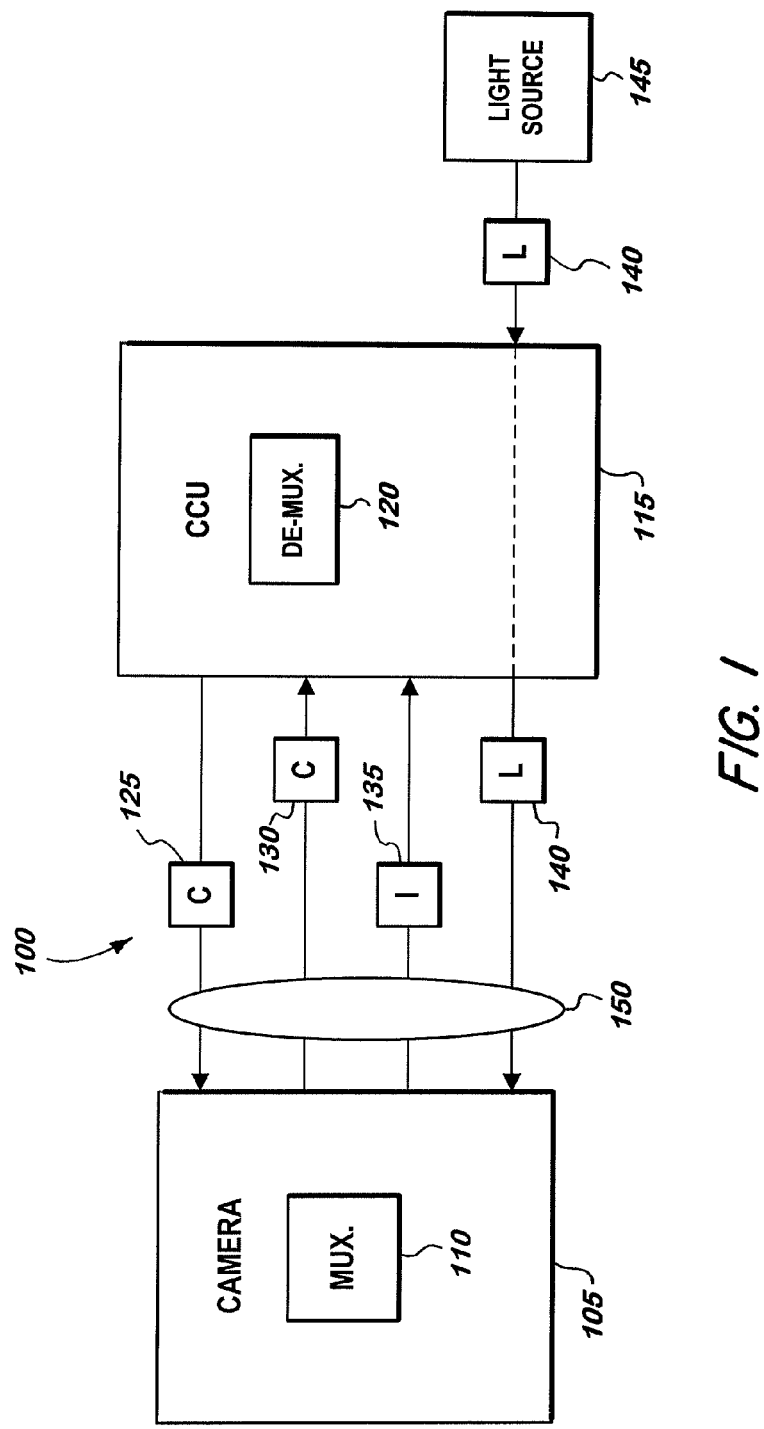
FIG. 1 is a block diagram of the video imaging system illustrating a camera, channel connections, a control unit, and an illuminating light source.

Referring now to the drawings, wherein like reference numerals designate corresponding structure throughout the views.

FIG. 1 illustrates an advantageous embodiment of the video imaging system 100. A camera head 105 is provided having a multiplexer 110 for multiplexing image data and control signals. A camera control unit 115 is provided with a multiplexer 120 for receiving and processing the multiplexed signal from the camera head 105. A command signal channel 125 is provided interconnecting camera head 105 and camera control unit 115. The command signal channel 125 allows command signals to be sent from the camera control unit 115 to the camera head 105. Command signals include any signal transmitted from the camera control unit to the camera head. A control signal channel 130 is provided interconnecting camera head 105 and camera control unit 115. The control signal channel 130 allows control signals to be sent from the camera head 105 to the camera control unit 115. Control signals include any signal transmitted from the camera head except image data, and may include signals such as: software programs, operating information, timing signal data, camera head identification information, camera use information and the like. An image data channel 135 is provided interconnecting camera head 105 and camera control unit 115. The image data channel 135 allows image data to be sent from the camera head 105 to the camera control unit 115 for processing.

Through multiplexer 110 the control signal 130 and the image data 135 are transmitted down the same physical pair of wires, and the command signal 125 is transmitted on a second pair of wires.

Alternatively, for further cable size reduction, the command signal may also be multiplexed with the control signal and image data and therefore be transmitted down the same physical wire, thereby reducing the number of wires to one pair. It is well known in the art that multiplexers 110 and 120 may perform both multiplexing and de-multiplexing functions. The video imaging system utilizes a digital serial protocol such as Low-Voltage Differential Signaling.

Further, it will be apparent to those skilled in the art that additional pairs of wires may be supplied for image data, control signals, and command signals for future data carrying requirements as new systems become available.

A light source guide 140 is also furnished to provide illuminating light from light source 145, through camera control unit 115, to camera head 105.

A single protective jacket 150 is also provided, for enclosing the command signal channel 125, the control signal channel 130, the image data channel 135, the light source guide 140, and any additional channels that may be utilized.

Figure 2:
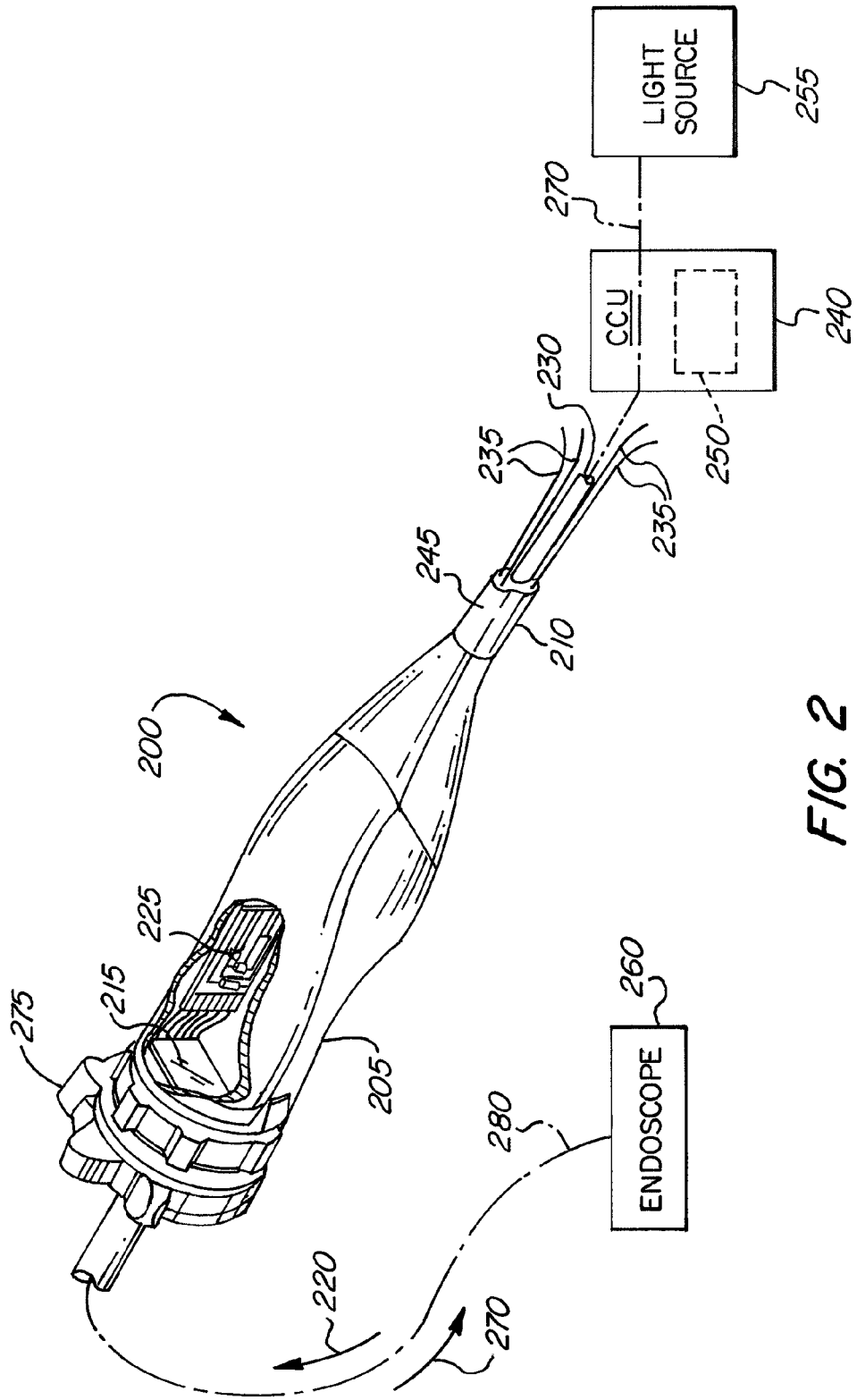
FIG. 2 is a depiction of a camera with a sectional view of an attached cable assembly, the control unit and the light source.

FIG. 2 illustrates an advantageous embodiment of the video imaging system 200. A camera head 205 is provided having a cable 210. In this embodiment, the cable 210 is permanently attached to the camera head 205. However, it is contemplated that the cable 210 may also be detachably connected to the camera head 205. The camera head 205 is equipped with an imager 215 for receiving photonic energy 220 reflected off an object (not shown). The camera head 205 is also equipped with a multiplexer 225 for multiplexing various signals generated by the camera head 205. The various signals may include for instance: image data generated by the imager 215, and control signals generated by the camera head 205. In FIG. 2, the video imaging system 200 further comprises an endoscope 260 wherein the camera head 205 receives light 270 from the light source 255 and transmits the light 270 to the endoscope 260. The light 270 is transmitted through the camera head 205. The light 270 is transmitted from the camera head 205 to the endoscope 260 through an intermediate coupling 275 mounted to the camera head 205 and a cable 280 for connecting the intermediate coupling 275 and the endoscope 260.

Figure 9:
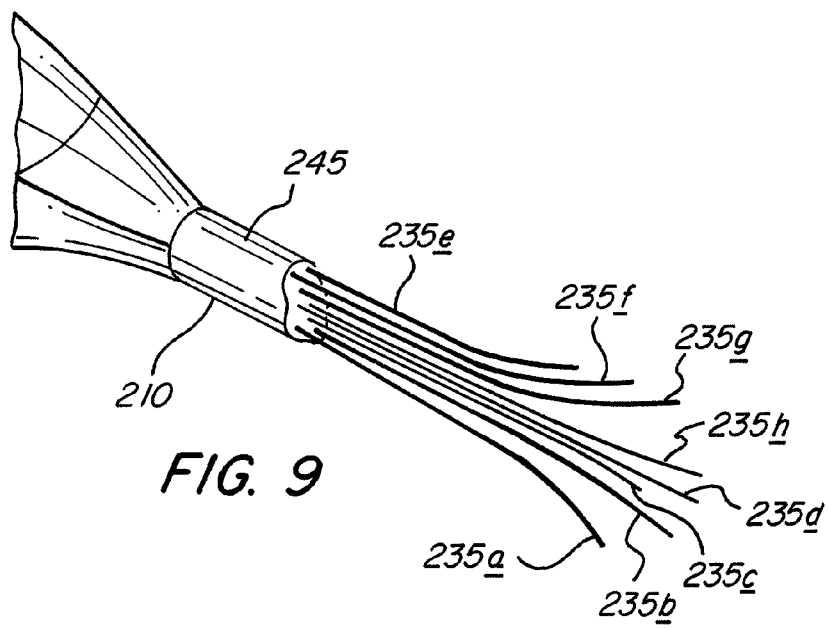
FIG. 9 is a depiction of a section of the camera of FIG. 2 showing four channels comprising eight electrical conductors.
Figure 10:
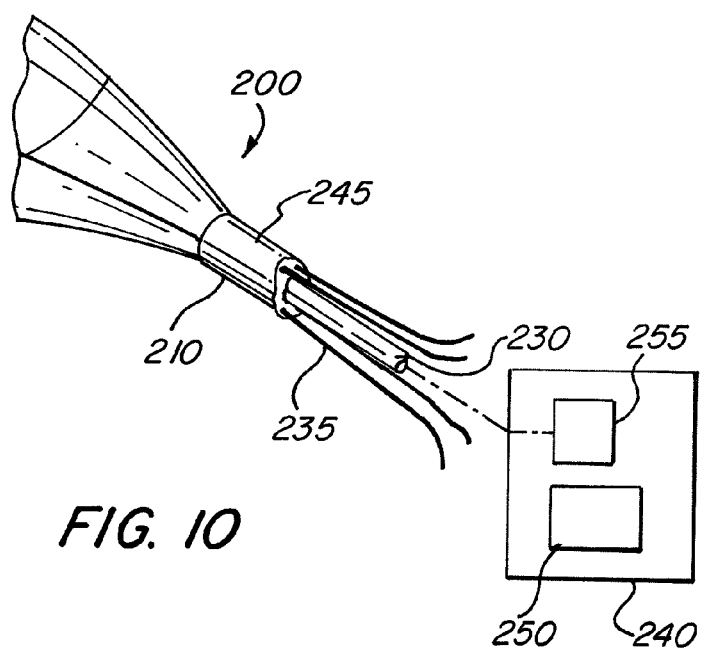
FIG. 10 is a depiction of a light source mounted within a control unit.

The cable 210 includes a light guide channel 230 for transmitting illuminating light to the camera head 205. The cable 210 further includes data channels 235 for transmitting data to and from the camera head 205 and the CCU 240. Four data channels 235 are depicted in FIGS. 2 and 10, however fewer or more data channels 235 may be utilized. Image data and control signals are multiplexed in the camera head 205 by the multiplexer 225 for transmission along data channels 235. One of the data channels 235 may be utilized for the multiplexed signal, or any number or combination of data channels 235 may be utilized. The cable 210 is also provided with a protective jacket 245, encasing the light guide channel 230 and the data channels 235. FIG. 9 depicts a section of the camera head of FIG. 2 showing four channels comprising eight electrical conductors 235a-h. Further in FIG. 2, the cable 210 engages the camera head 205 so as to direct light 270 longitudinally completely through the camera head 205. FIG. 10 is a depiction of a light source 255 mounted within a camera control unit 240.

In this advantageous embodiment it is contemplated that the CCU 240 may also be provided with a multiplexer 250 for multiplexing command signals, and for demultiplexing the image data and control signals sent from the camera head 205. It is contemplated that multiplexers 225 and 250 may both provide both multiplexing the demultiplexing functions. A light source 255 is also provided for generating illuminating light for the transmission by the light guide channel 230 to the camera head 205. The cable 210 is detachably connected to the CCU 240 as disclosed in FIGS. 3-8.

Figure 3:
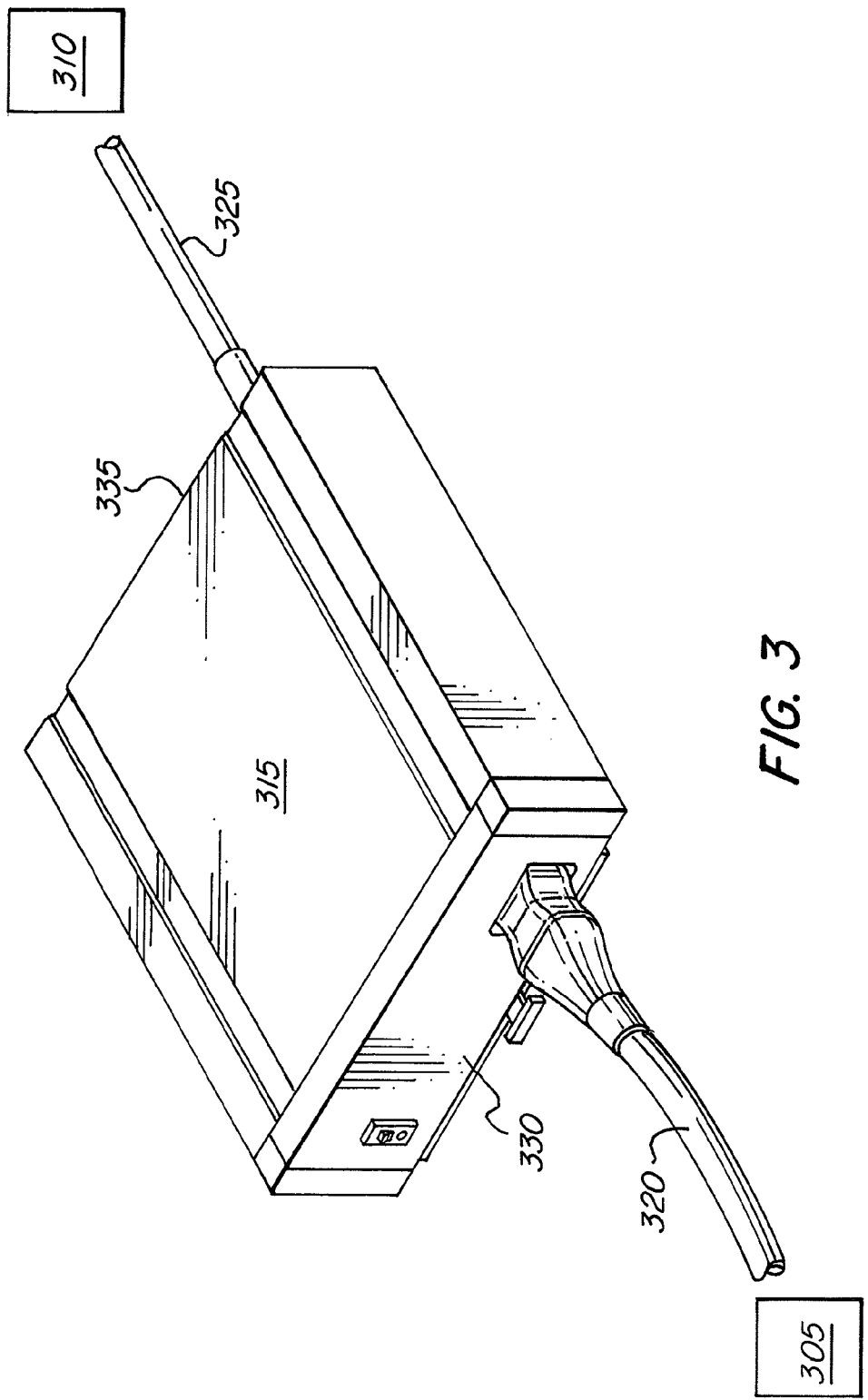
FIG. 3 is a depiction of the control unit, the receptacle, the connector attached to the cable, and the light source.

Referring to FIGS. 3-8, and particularly FIG. 3, a connector assembly for an endoscope assembly provides a connection between a camera head 305 and a source of light 310 through a CCU 315 having a front portion 330 and a rear portion 335. A cable 320 extending from the camera head carries a light source guide and at least one wire pair transmitting electronic signals between the CCU and the camera head. A light source cable 325 extends from the light source 310 through the CCU and directly engages the cable 320 in the CCU.

Referring to FIG. 4, the connector assembly includes a plug 405 provided with a molded body 410. A light connector 415 extends from a front surface 420 of the molded body 410, whereas an electrical connection, which is mostly encased in the molded body 410, has a keyed edge connector 425 projecting beyond the front surface 420. As clearly seen in FIG. 4, the light connector 415 and the keyed edge connector 425 extending through the plug 405 are in a fixed spatial relationship.

The keyed edge connector 425 can be selected from a great variety of electrical connectors and, in the present case, is shown as a printed wiring board. The keyed edge connector 425 preferably terminates in the same plane as the light connector 415. However, it is contemplated within the scope of the invention to provide an arrangement where the keyed edge connector 425 and the light connector 415 extend from the front surface 420 of the molded body 410 at different distances. Such structure provides for mating components of the receptacle to be similarly positioned with respect to one another. The light connector 415 is shown above the keyed edge connector 425. However, it is possible to arrange the components in many different arrangements. It is however, advantageous to maintain a fixed spatial relationship as to the components in utilizing the various arrangements.

As further shown in FIG. 4, the molded body 410 has keying surfaces 430 for the plug as well as protection for the light connector 415 and the keyed edge connector 425 by extending from the front surface 420 beyond these connectors. The plug 405 is introduced through the front side 330 of the CCU (FIG. 3) into a receptacle opening 435. Each of the keying surfaces 430 has the geometry that allows the plug to enter the receptacle only in a predetermined spatial position. Exclusively, for illustrative purposes, each of the keying surfaces 430 of FIG. 4 has two straight portions 440, 445 inclined with respect to one another.

The keying surfaces 430 are shaped and sized to place the plug 405 in a unique spatial position with respect to a receptacle 450 by extending complementary to an inner peripheral surface 455 of the opening 435 at the entry point for the plug 405. The plug is advanced 460 into the receptacle 450 as indicated to provide engagement between light connector 415 and keyed edge connector 425 with optical component 505 and electrical component 510 respectively, as shown in FIG. 5. The position of the optical component 505 and electrical component 510 is a mirror image of the configuration of the light connector 415 keyed edge connector 425 respectively. Furthermore, a grounding plate 605, seen in FIG. 6, is provided with a plurality of spaced-apart, resilient fingers 610 seen in FIGS. 5 and 6, which extend slightly above a bottom edge 515 of the opening 435 seen in FIG. 4.

The receptacle 450 has a housing 615, as seen in FIG. 6, provided with a detachable front panel 620. The front panel 620 has a front flange 625 lying flush with the front side 330 of the CCU when assembled. To provide a correct position of the front panel 620 with respect to the housing 615, each of the sides 630 has an elongated recess 635 receiving a respective lug 640 formed on the housing 615.

The housing 615 receives an optical connector component of the light source cable 325 extending through the rear portion 335 of the CCU and the light connector 415 and the keyed edge connector 425 of the plug 405. A chamber 645 is sized so that the molded body 410 of the plug 405 extends at its full length into the receptacle 450 in an engaged position where the light connector 415 and the keyed edge connector 425 of the plug 405 engage respective components of the receptacle 450.

Figure 7:
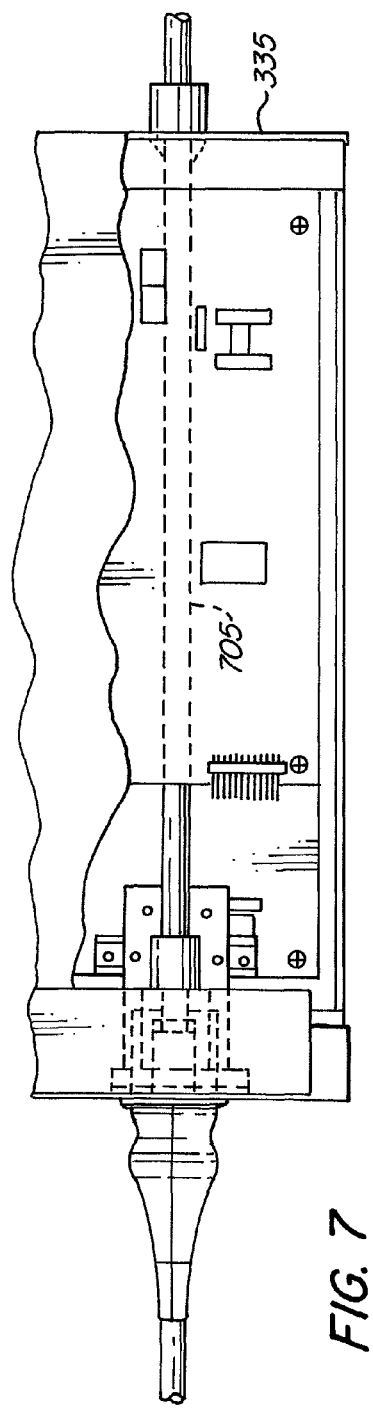
FIG. 7 is a top section view of the control unit of FIG. 1 depicting the light source guide entering the control unit from the rear and connecting with the cable through the receptacle.
Figure 8:
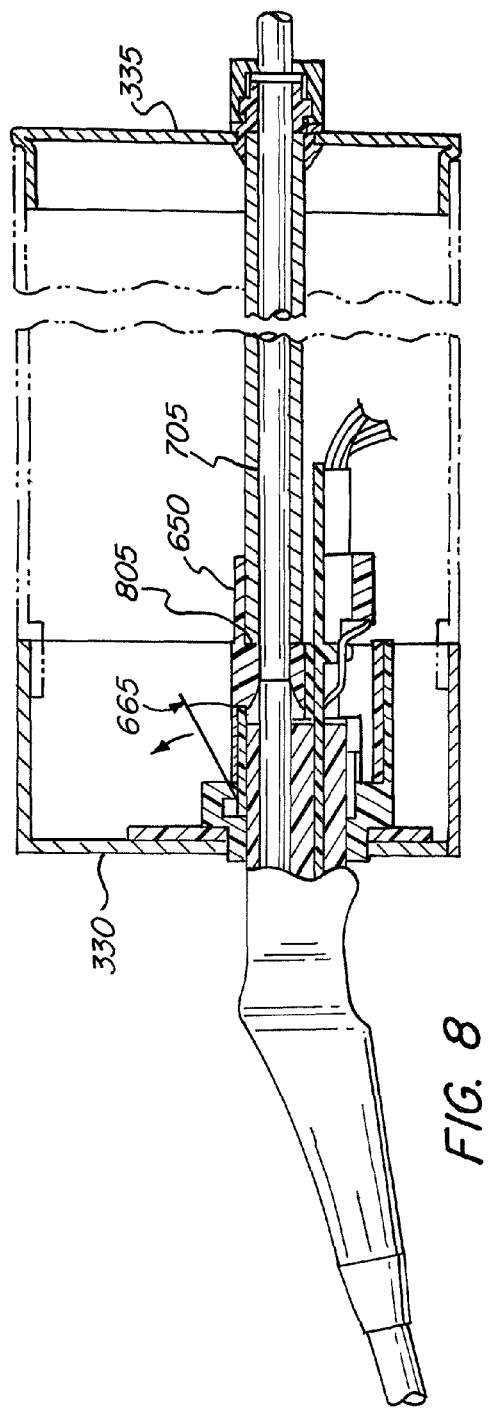
FIG. 8 is a side section view of the control unit of FIG. 1 depicting the light source guide entering the control unit from the rear and connecting with the cable through the receptacle.

The housing 615 is further provided with a collar 650 extending toward the rear portion 335 of the CCU 315 and receiving a guide element 705 as seen in FIG. 7, that linearly spans the distance between the rear portion 335 of the CCU 315 and the receptacle 450. An inner end of the guide element 705 slides against the collar 650 and abuts a seat 805 as seen in FIG. 8, of the housing 615 of the receptacle 450. An end of the light source cable 325 having an optical connection component extends beyond the guide element 705 and terminates in a rear wall 655 of the chamber 645. Thus, the light source cable 325 is mounted within the receptacle 450 in a fixed spatial position and is aligned with the cable 320 after the molded body 410 of the plug 405 is registered with the opening 435 of the front panel 620.

To provide an electrical connection between the camera head and the remaining CCU components, the receptacle 450 includes an electrical component 510 comprising a socket 660. The socket 660 is in the same fixed spatial relationship with the optical component 505.

To prevent the high intensity light from the source of light 310 from escaping the CCU 315, the receptacle 450 is provided with a light deflector 665, which is mounted to block the light from exiting the CCU 315 from the light source cable 325 when the plug 405 is withdrawn from the receptacle 450. A bottom portion 675 bridges spaced apart walls 670 of the light deflector 665. The deflector 665 is sized so that the keying surfaces 430 of the plug 405 contacts the bottom portion 675 as the plug 405 is advanced into the receptacle 450. The light deflector 665, which is pivotally mounted by means of a pin 680 extending between the spaced apart walls 670 and mounted on the housing 615 of the receptacle 450, swings out of a light path. As the plug is withdrawn from the receptacle 450, the light deflector 665 swings back into the light path to confine the light inside the CCU 315.

To ensure that the pin 680 is not displaced from the housing 615, a flange 685 provided on the front panel 620 covers a recessed portion 690. Thus, the pin 680 may rotate between the bottom of the chamber 645 and the flange 685. The chamber 645 is dimensioned to have the rear wall 655 juxtaposed with an edge 695 of the spaced apart walls 670 along the entire path of the light deflector 665, as the plug 405 is being advanced or withdrawn from the receptacle 450. Furthermore, the rear wall 655 has a curvature of the same radius as the edge 695. As shown, the spaced apart walls 670 of the light deflector 665 have a triangular cross-section; however, any other cross-section allowing the light deflector 665 to swing into and out of the light path can be easily implemented. Only one advantageous embodiment is illustrated in the figures, however it will be apparent to those skilled in the art that many different embodiments may be possible for implementing the light deflector 665. For instance, the light deflector may be rotatable, to rotate into the path of the light as shown, but it may also be slideable, or alternatively a sensor for sensing the presence of the plug 405 in the receptacle 450, may act to disconnect, obstruct, attenuate or turn off the source of light 310 upon removal of the plug 405 from the receptacle 450. Any of these or other methods may be utilized to prevent the light from escaping upon disconnection.

Figure 11:
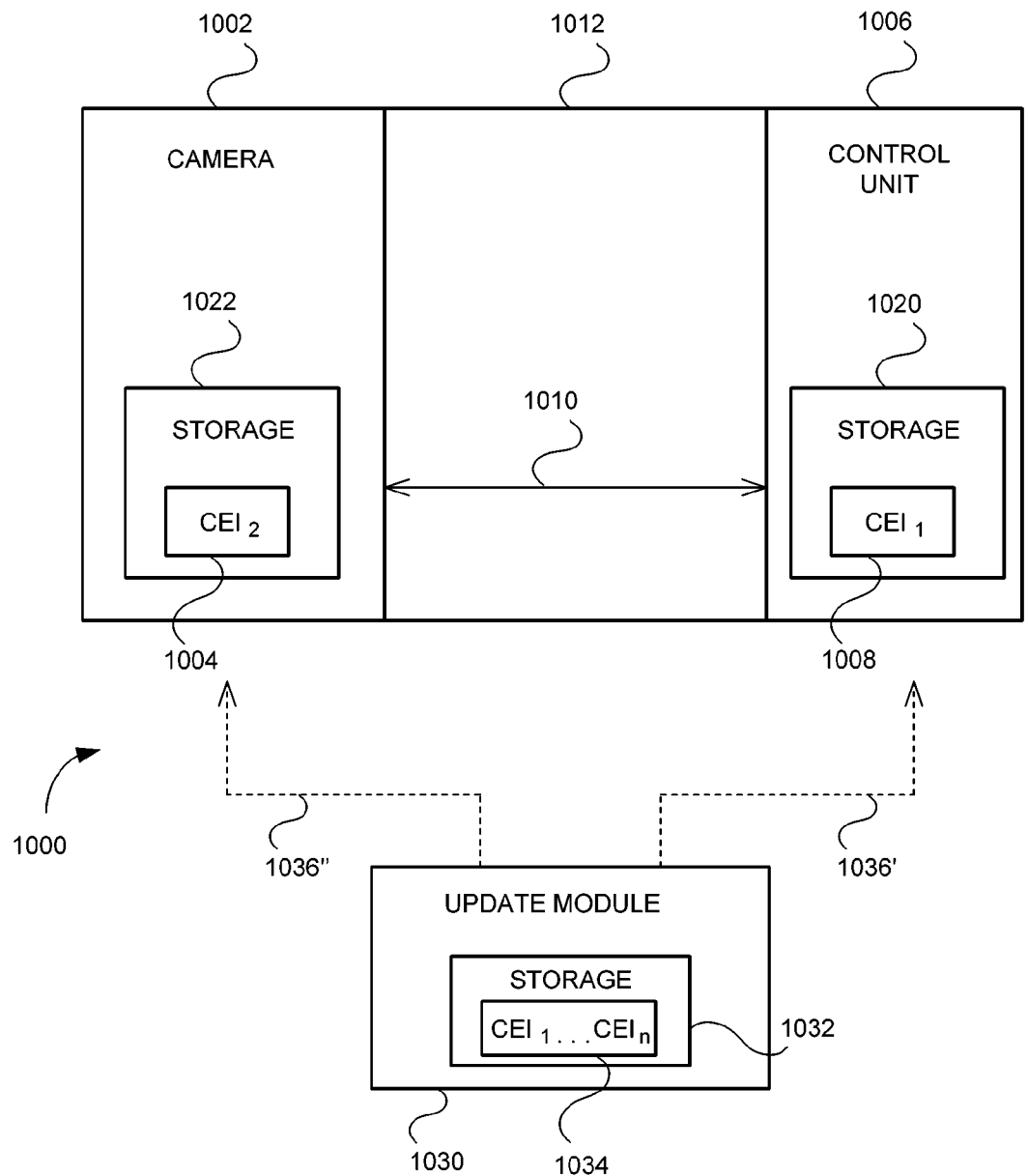
FIG. 11 is a block diagram of a camera assembly showing a control unit having a first set of data processing instructions and coupled to a camera having a second set of data processing instructions and an update module.

In FIG. 11 a camera assembly 1000 is shown. The camera assembly 1000 comprises at least one camera 1002 configured to generate electronic imaging data 1010. The electronic imaging data 1010 includes for example, the aforementioned command and control signals and image data of FIG. 1. A control unit 1006 is detachably coupled at 1012 to the at least one camera 1002 and receptive of the imaging data 1010. A first set of data processing instructions ($CEI_1$) 1008 are stored in storage 1020 in the control unit 1006 for processing the imaging data 1010. A second set of data processing instructions ($CEI_2$) 1004 reside in storage 1022 on the at least one camera 1002 for processing the imaging data 1010 based upon the first set of prescribed imaging functions. The aforementioned processing of the imaging data 1010 includes, for example, sending, receiving, storing, sorting, ordering, digitizing, multiplexing or otherwise performing signal or data processing on the imaging data 1010.

Update module 1030 is also illustrated in FIG. 11. Update module 1030 includes storage 1032 having updated data processing instructions ($CEI_1 \ldots CEI_n$) 1034 located thereon for updating of the various data processing instructions. Two connections are shown in dashed lines 1036' and 1036" illustrating that update module 1030 may be connected to either camera 1002 or control unit 1006 for updating of the various data processing instructions ($CEI_1 \ldots CEI_n$). It should be noted that update module 1030 may further be indirectly coupled to camera 1002 through control unit 1006.

Update module 1030 may be coupled to camera 1002 and/or control unit 1006 either by direct connection or wirelessly. It is contemplated that a wireless connection may comprise but is not limited to for instance, an infrared coupling, but may also include any other suitable coupling means such as RF, inductive, and other wireless methods. Alternatively, if the coupling means is a direct connection, the update module 1030 may comprise for instance, a card that is inserted into control unit 1006 and/or camera 1002. In either instance, update module 1030 may be used to provide updated data processing instructions to camera 1002 and/or control unit 1006.

It is further contemplated that update module 1030 may be utilized to ascertain the update and user rights for instance, authorized the user for a particular camera 1002 and/or control unit 1006. This is advantageous because a technician may visit a client and with the update module 1030, ascertain what if any updates and/or upgrades the user is entitled to based upon reading data that may be stored on camera 1002 and/or control unit 1006 and then provide any additional functionality and/or updates the user is entitled to. This provides for minimal down-time for routine software upgrades which allows the user to maintain fewer cameras in stock because they do not have to be sent out to the factory for upgrading. The automatic authorization reading functionality also means that fewer mistakes will be made by the technician as the update module 1030 will determine what rights the user has contracted.

It is further contemplated that update module 1030 will gather from the camera 1002 and/or control unit 1006 data that may include for instance but is not limited to the software version number, model number, serial number, date of manufacture, service dates, software upgrade dates, owner data, and device location of camera 1002 and/or control unit 1006. This information may be advantageously stored on said update module 1030 in storage 1032 for later transmission to a computer (not shown). It is also contemplated that this camera and/or control unit data may be directly transmitted over a network to a computer system for compliance with governmental regulations. In any event, the update module 1030 may be utilized to gather this information for reporting purposes, which may take the form of for instance, a report.

Figure 12:
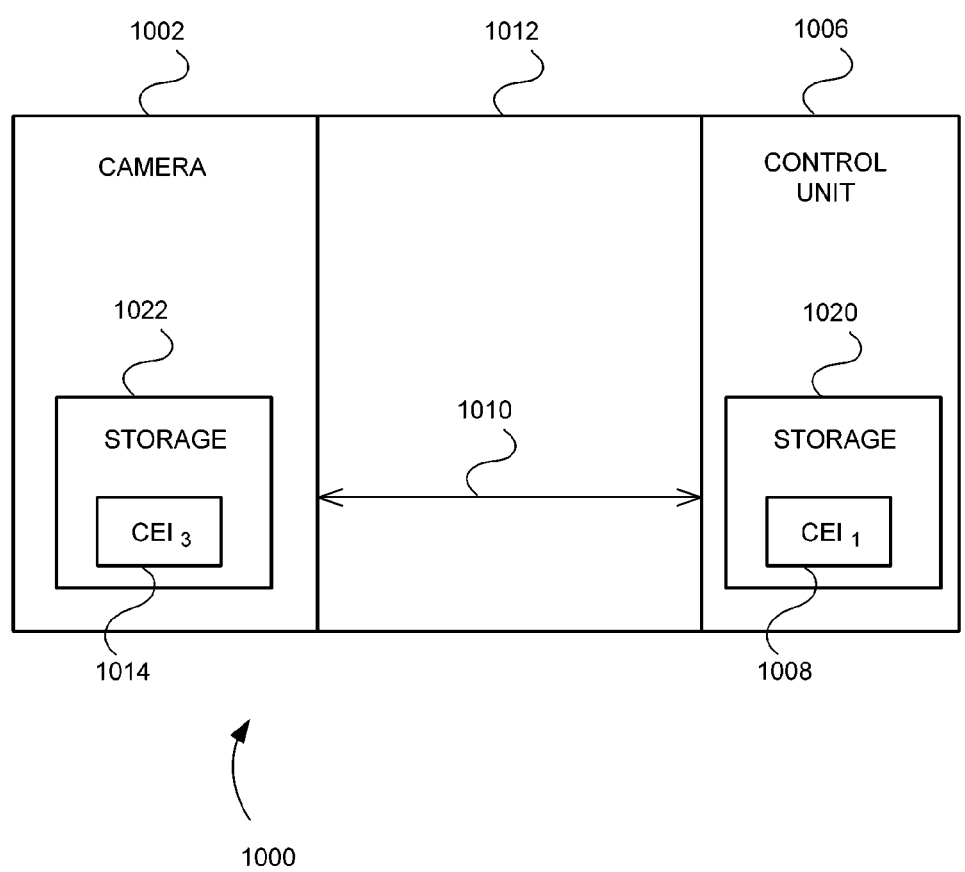
FIG. 12 is a block diagram of the camera assembly of FIG. 11 showing an interchangeable third set of data processing instructions.

In FIG. 12, a third set of data processing instructions ($CEI_3$) 1014 is interchangeable with the second set of data processing instructions 1004 and are operative in processing the imaging data 1010.

In general, the camera includes imaging functions characteristic of the camera 1002 such as camera exposure (shutter speed), camera focus, camera zoom, camera rotation or photo dynamic diagnosis. The electronic imaging data 1010 is conveyed between the camera 1002 and the control unit 1006 by way of the command signal, control signal and image data channels 125, 130, 135 of FIG. 1. The camera 1002 can be configured to operate differently based upon the instructions that are stored in the camera 1002. In particular the camera is configured to operate according to a set of data processing instructions specific to each camera 1002 and stored in each camera 1002. This allows each camera 1002 to provide the data processing instructions necessary to support any unique features that the camera may have. Multiple camera types may be used. Camera types comprise a combination of characteristics, such as: standard or direct coupling interface (DCI), National Television System Committee (NTSC) or Phase Alternating Line (PAL) one chip, NTSC or PAL three chip or progressive scan sensors, photodynamic diagnosis (PDD) enabled or disabled, rotation, zoom and or focus enabled or disabled. Each camera type is configured to operate differently based upon the set of data processing instructions stored therein.

As seen in FIGS. 11 and 12 the second set of data processing instructions 1004 and the third set of data processing instructions 1014 are interchangeable and both compatible with the first set of data processing instructions 1008. Thus, should the camera 1002 be used in different environments, the interchangeable data processing instructions 1004, 1014 can be changed as needed to suit the environment. For example, if the camera 1002 is used in arthroscopic surgery, the second set of data processing instructions 1004 would be operative in the camera 1002 (FIG. 11). However, if the camera 1002 is used in intestinal surgery, the third set of data processing instructions 1014 would be operative in the camera 1002 (FIG. 12).

Figure 13:
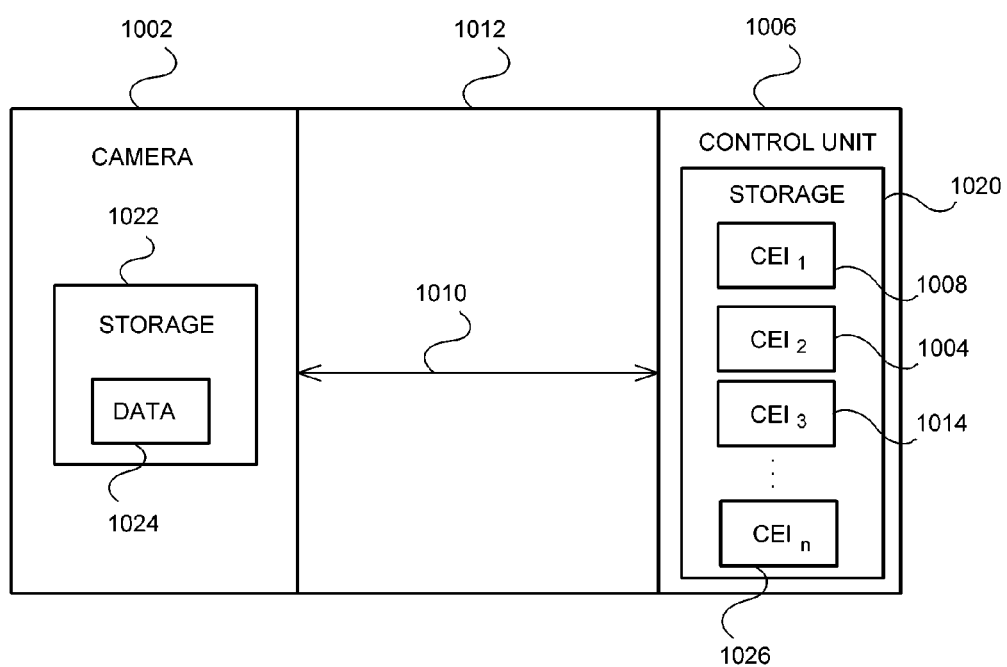
FIG. 13 is a block diagram of the camera assembly of FIGS. 11 and 12 showing interchangeable data processing instructions.

In FIG. 13 a plurality of data processing instructions (108, 1004, 1014, 1026) are stored in storage 1020. Upon connection of camera 1002 with control unit 1006, control unit 1006 reads camera data 1024 and determines the correct data processing instructions to utilize. It is contemplated that the selected data processing instructions may be utilized on control unit 1006, on camera 1002 and/or both. It is further contemplated that any number of data processing instructions may be stored on storage 1020. While storage 1020 is shown located in control unit 1006, it is yet further contemplated that the storage may be local or remote to control unit 1006, for instance but not limited to connection over a network or internetwork.

It should further be noted that although updated module 1030 (FIG. 11) is not illustrated in FIGS. 12 and 13, it is contemplated that it is fully compatible those systems providing upgraded functionality and updated data according to the user's licensed rights.

Figure 14:
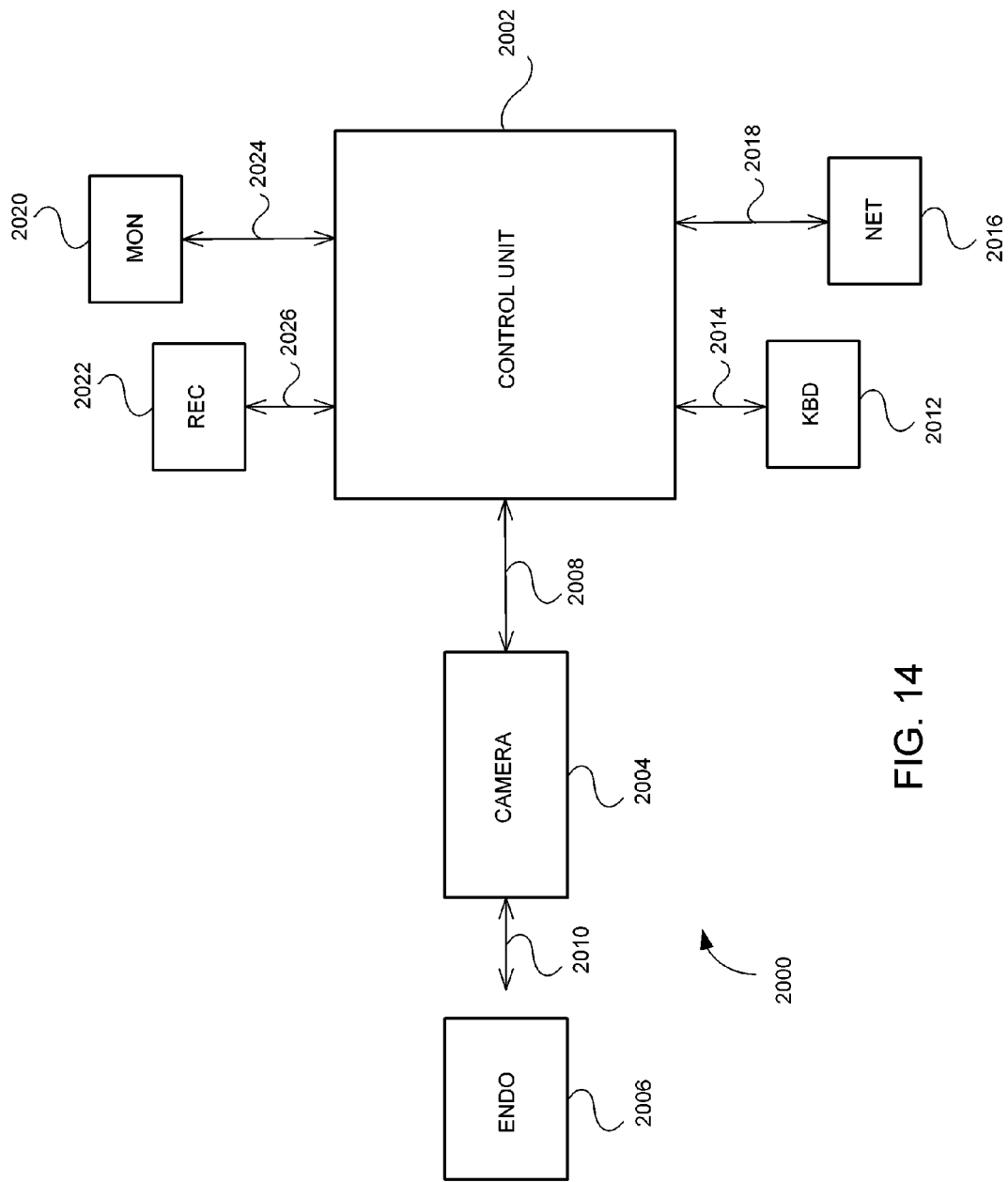
FIG. 14 is a block diagram of the camera assembly of FIGS. 11, 12 and 13 showing the control unit and camera in communication with peripheral devices.

FIG. 14 is a schematic representation of a camera assembly 2000 of FIGS. 11, 12 and 13 showing the control unit 2002 in communication with certain peripheral devices, such as a keyboard (KBD) 2012, a communications network (NET) 2016, a monitor (MON) 2020 and a recorder (REC) 2022. A camera 2004 is in communication 2010 with an endoscope (END) 2006 or other medical device and with the control unit 2002 at 2008.

Thus, based upon the foregoing description, a camera assembly is disclosed wherein a camera is adapted to generate electronic image data. A control unit is detachably coupled to the camera and receptive of the image data. A plurality of data processing instructions for processing the imaging data is stored in the camera and/or the control unit. When the camera is coupled to the control unit, the plurality of data processing instructions transfer the imaging data from the camera to the control unit.

Although the invention has been described with reference to a particular arrangement of parts, features and the like, these are not intended to exhaust all possible arrangements or features, and indeed many other modifications and variations will be ascertainable to those of skill in the art.

What is claimed is:

1. A camera assembly, comprising:
   a camera for generating image data;
   a control unit detachably coupled to said camera and receptive of the image data, said control unit having a network connection;
   a storage accessible by said control unit;
   a first set of data stored on said storage;
   a second set of data stored on said storage;
   wherein when said camera is coupled to said control unit, said camera is identified and one of said first set or said second set of data is selected based on the camera identification for processing the image data.

2. The camera assembly according to claim 1 wherein the image data is stored on said control unit.

3. The camera assembly according to claim 1 wherein the first set of data comprises a device driver.

4. The camera assembly according to claim 1 further comprising an endoscope in communication with the said camera.

5. The camera assembly according to claim 1 wherein said camera is coupled to said control unit via a cable comprising both an electrical and an optical channel.

6. The camera assembly according to claim 1 wherein said camera is selected from the group consisting of: a single chip imager and a three chip imager, and combinations thereof.

7. The camera assembly according to claim 1 wherein said control unit includes a processor field programmable gate array and a formatter field programmable gate array.

8. The camera assembly according to claim 7 wherein when no camera is plugged into the control unit the control unit loads a base field programmable gate array configuration code to at least one of the formatter field programmable gate array or the processor field programmable gate array.

9. A camera assembly, comprising:
   a camera for generating image data;
   a control unit detachably coupled to said camera and receptive of the image data;
   camera operating instructions stored on said camera; and
   control unit operating instructions stored on said control unit;
   wherein when said camera is coupled to said control unit, said camera operating instructions on said camera cooperate with said control unit operating instructions on said control unit to transfer and process the image data from said camera to said control unit;
   wherein the control unit operating instructions are capable of configuring both a formatter field programmable gate array and a processor field programmable gate array and the image data is stored on said control unit.

10. The camera assembly according to claim 9 wherein the control unit operating instructions comprise a device driver.

11. The camera assembly according to claim 9 further comprising an endoscope in communication with the said camera.

12. The camera assembly according to claim 9 wherein said camera is coupled to said control unit via a cable comprising both an electrical and an optical channel.

13. The camera assembly according to claim 9 wherein said camera is selected from the group consisting of: a single chip imager and a three chip imager, and combinations thereof.

14. The camera assembly according to claim 9 wherein said control unit operating instructions comprise a plurality of camera specific data processing instructions and when same camera is coupled to said control unit, the control unit selects the correct camera specific data processing instructions to use based on identification of the connected camera.

15. The camera assembly according to claim 9 wherein when no camera is plugged into the control unit the control unit loads a base field programmable gate array configuration code to at least one of the formatter field programmable gate array or the processor field programmable gate array.

16. A camera assembly, comprising:
a camera for generating image data;
a control unit detachably coupled to said camera and receptive of the image data, said control unit having a network connection;
a storage accessible by said control unit;
a plurality of sets of image processing data stored on said storage;
a set of data processing data stored on said storage;
wherein when said camera is coupled to said control unit, said camera is identified and one of said plurality of image processing data is selected based on the camera identification for processing the image data and said set of data processing data is used for processing said image data.

17. The camera assembly according to claim 16 wherein said camera is selected from the group consisting of: a single chip imager and a three chip imager, and combinations thereof.

18. The camera assembly according to claim 16 wherein said plurality of sets of image processing data are capable of configuring both a formatter Field Programmable Gate Array and a processor Field Programmable Gate Array and the image data is stored on said control unit.

19. The camera assembly according to claim 18 wherein when no camera is plugged into the control unit the control unit processing instructions download a base field programmable gate array configuration code to at least one of the formatter field programmable gate array or the processor field programmable gate array.

* * * * *